(12) United States Patent
Baid et al.

(10) Patent No.: US 12,397,106 B2
(45) Date of Patent: Aug. 26, 2025

(54) SAFETY MECHANISM FOR A HUBER NEEDLE ASSEMBLY

(71) Applicant: POLY MEDICURE LIMITED, Faridabad-Haryana (IN)

(72) Inventors: Rishi Baid, New Delhi (IN); Manjit Singh, Faridabad-Haryana (IN)

(73) Assignee: POLY MEDICURE LIMITED, Faridabad-Haryana (IN)

( * ) Notice: Subject to any disclaimer, the term of this patent is extended or adjusted under 35 U.S.C. 154(b) by 1095 days.

(21) Appl. No.: 17/419,007

(22) PCT Filed: Dec. 27, 2019

(86) PCT No.: PCT/IB2019/061389
§ 371 (c)(1),
(2) Date: Jun. 28, 2021

(87) PCT Pub. No.: WO2020/136610
PCT Pub. Date: Jul. 2, 2020

(65) Prior Publication Data
US 2022/0062539 A1    Mar. 3, 2022

(30) Foreign Application Priority Data

Dec. 27, 2018  (IN) .............................. 201811049316

(51) Int. Cl.
*A61M 5/158* (2006.01)
(52) U.S. Cl.
CPC ..... *A61M 5/158* (2013.01); *A61M 2005/1581* (2013.01); *A61M 2005/1587* (2013.01); *A61M 2205/3334* (2013.01)

(58) Field of Classification Search
CPC .......... A61M 5/158; A61M 2005/1581; A61M 2005/1587; A61M 2205/3334;
(Continued)

(56) References Cited

U.S. PATENT DOCUMENTS

| 5,858,001 A | 1/1999 | Tsals et al. | |
| 2003/0069546 A1* | 4/2003 | Sandstrom | A61M 5/158 |
| | | | 604/263 |

(Continued)

FOREIGN PATENT DOCUMENTS

| WO | 2007/079115 A2 | 7/2007 |
| WO | 2013/049568 A1 | 4/2013 |

OTHER PUBLICATIONS

International Search Report and Written Opinion issued by the European Patent Office for corresponding application PCT/IB2019/061389 dated Mar. 31, 2020.

(Continued)

*Primary Examiner* — Bhisma Mehta
*Assistant Examiner* — Nelson Louis Alvarado, Jr.
(74) *Attorney, Agent, or Firm* — Bradley Arant Boult Cummings LLP; Henry B. Ward, III

(57) ABSTRACT

The present invention relates to a needle having safety mechanism for a huber needle assembly in which the safety mechanism comprises a needle hub, a base, a huber needle slidably disposed through the needle hub, a wing holder having two wings at the opposite end of the wing holder, a connector which connects the needle hub and the base for protecting the tip of the huber needle.

10 Claims, 17 Drawing Sheets

(58) Field of Classification Search
CPC .... A61M 2005/1585; A61M 2205/195; A61M 5/1626; A61M 39/0208; A61M 2005/1586
See application file for complete search history.

(56) References Cited

U.S. PATENT DOCUMENTS

2007/0149920 A1* 6/2007 Michels ............... A61M 5/158
604/93.01
2013/0085449 A1* 4/2013 Saulenas ............. A61M 5/158
604/164.01

OTHER PUBLICATIONS

First Examination Report issued by the Indian Patent Office for Indian Patent Application No. 201811049316, dated Feb. 3, 2021.

* cited by examiner

SAFETY MECHANISM FOR A HUBER NEEDLE ASSEMBLY

FIELD OF THE INVENTION

The invention generally relates to needle assemblies having safety mechanism for subcutaneous injections. More particularly, the invention relates to huber needle assemblies having a safety mechanism.

BACKGROUND OF THE INVENTION

A Huber needle assembly is generally known in the art. Conventional Huber needle assemblies are widely used in hospitals and are often used in conjunction with implanted ports mostly used to treat hematology and oncology patients. Such Huber needle assemblies provide non-coring Huber needles that are used to administer chemotherapy, IV fluids, medications, total parenteral nutrition, or to transfuse blood products through the implanted ports. The implanted port contains a self-sealing septum that seals around the non-coring needle, holds the needle in place, and allows for multiple accesses by a Huber needle.

In the area of subcutaneous medication device access (port), where Huber needle assembly is used, an existing safety device offer a margin of protection from accidental needle sticks when removing the needle, or "sharp," from the port. One danger from de-accessing a subcutaneous port is the result of how the port itself is constructed. The port is made up of metal or plastic material with a pierceable area, often made of a silicone compound, through which access is made by a Huber needle to the vascular system for the purpose of infusing medication into the body. The port is implanted within a cavity formed in the patient, such as in the chest area, and sutured to underlying tissue. From time to time, it is desirable to refill the port via the septum and/or provide an external source of fluid, e.g., IV access. One type of device used to refill an implanted port is generally known as a Huber needle.

The Huber needle is specially designed to reduce the possibility of mechanically damaging and/or removing a portion of the pierceable area as it is punctured, and which is referred to as "coring." This coring limits the number of times a port can be accessed. To combat this damage and extend the useful life of the port, the silicone compound is inserted under pressure into the device. It is this pressure that is the cause of the danger to the medical practitioner removing the needle used to cannulate the port.

Conventional Huber needle assemblies are designed for safety of patients. They do, however, present considerable risks to the medical practitioners using them. A conventional Huber needle assembly requires two hands to extract its Huber needle from an implanted port. One hand is used to stabilize the implanted port, while the other hand is used to withdraw the needle. The force required to withdraw the needle from the self-sealing septum of the implanted port can cause the needle to rebound and stick the user. This may result in transfer of a blood-borne pathogen to the user. Further, it may expose the user to hazardous drugs.

Although several alternate Huber needle assemblies are available, a need still exists for a Huber needle assembly with safety features that minimize the risk of exposure to blood-borne pathogens or drugs or accidental needle pricks.

SUMMARY AND OBJECTS OF THE INVENTION

A primary object and advantage of the present invention is to provide a huber needle assembly which is efficient, effective and simple in its construction and use.

It is another object of the present invention to provide a huber needle assembly with safety mechanism.

It is another object of the present invention to provide a huber needle assembly with safety mechanism having automatic control features.

It is another object of the present invention to provide a Huber needle assembly which provides better protection against accidental pricking by the needle tip.

It is another object of the present invention to provide a Huber needle assembly which is inexpensive to manufacture.

It is another object of the present invention to provide a compact design for a huber needle assembly.

In accordance with one of the embodiments of the present invention, a huber needle assembly having a safety mechanism comprising a main body. The main body comprises a needle hub and a base, the needle hub having distal end and a proximal end, a huber needle is slidably disposed across the needle hub through the needle fitment area, the huber needle comprising a tip, a wing holder at the base having two wings at the opposite end of the wing holder, a conduit through which an axle is placed to connect the base with the needle hub, a connector is slidably arranged across the space provided between the distal end and the proximal end of the needle hub through a lever and the chamber at the base through a lever, the dimension of the space is according to the length of the connector, so that the connector is axially arranged across the space of the needle hub at the ready position of the huber needle, the distal end of the needle hub having a flip. The connector is attached through a lever within the space which connect the needle hub and base. The needle hub having a channel through which huber needle passes and which is connected to the tube. The one end of the tube is connected to the proximal end of the needle hub and other end of the tube is connected to the luer lock, the luer lock having female luer in order to make leak-free connections between two parts. The tube has a clamp to regulate the flow of liquid through the tube.

According to another embodiment, the present invention relates to a huber needle assembly having a safety mechanism according to the present invention. The main body comprises a huber needle assembly with a safety mechanism for guarding the huber needle tip against accidental pricking. The main body comprising a needle hub and a base, the needle hub which contain the huber needle with a needle tip, the needle hub having distal end and a proximal end, the distal end of the needle hub having a flip, a wing holder having two wings at the opposite end of the wing holder, the base is connected to the needle hub through the axle. A connector according to another embodiment of the present invention, which connect the needle hub and base. The connector is slidably arranged across the both side the needle hub through the lever which is attached at the chamber of the base. The needle hub having a channel through which needle passes and connected to the tube. The one end of the tube is connected to the proximal end of the needle hub and the other end of the tube is connected to the luer lock having female luer in order to make leak-free connections between two parts. The tube has a clamp to regulate the flow of liquid across supply tube.

BRIEF DESCRIPTION OF THE ACCOMPANYING DRAWINGS

The foregoing and other objects, features, and advantages of the invention will be apparent from the following detailed description taken in conjunction with the accompanying drawings, wherein.

DETAILED DESCRIPTION OF THE INVENTION

Figure 1:
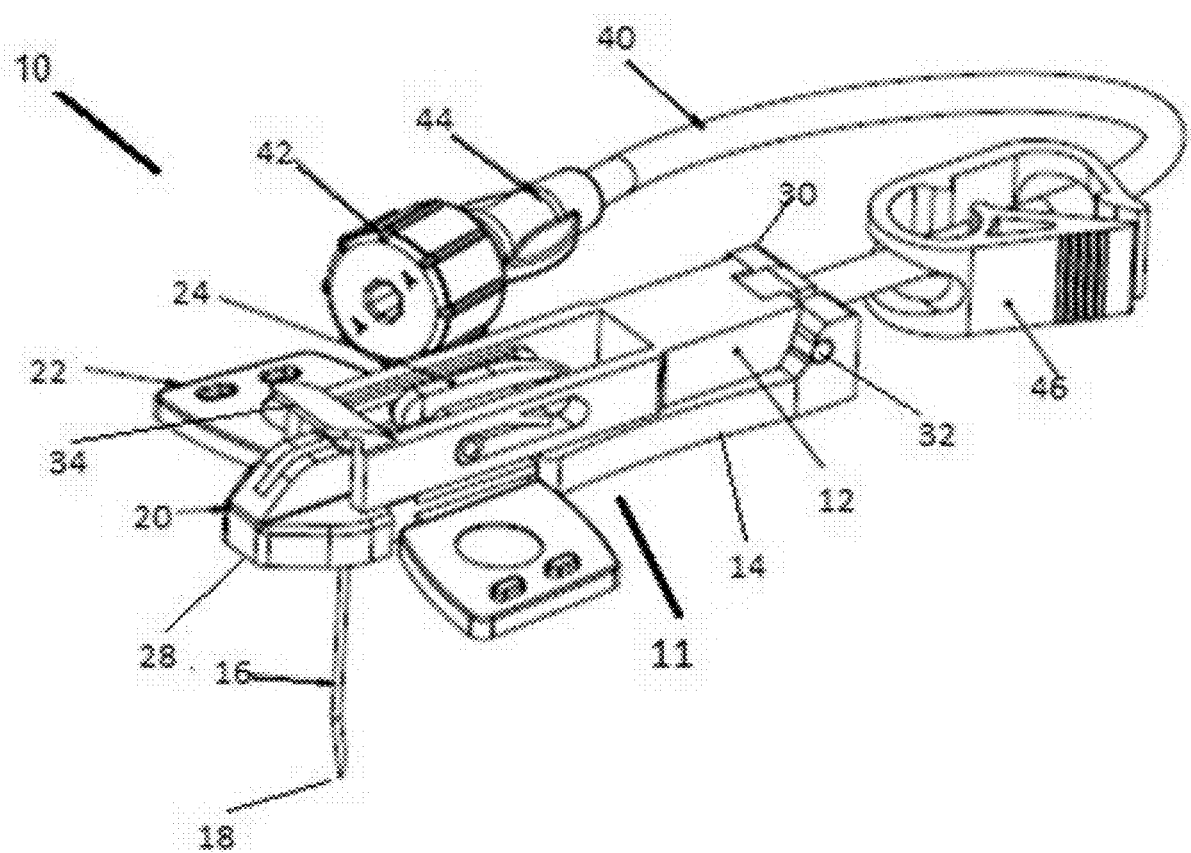
FIG. 1 illustrates a huber needle assembly according to one of the embodiments of the present invention.

Embodiments of the presently disclosed invention will now be described in detail with reference to the drawings wherein like reference numerals designate identical or corresponding elements. In the drawings and in the description, the term "proximal", "bottom", "down" or "lower" refers to a location on the device that is closest to the medical practitioner using the device and farthest from the patient in connection with whom the device is used when the device is used in its normal operation. Conversely, the term "distal", "top", "up" or "upper" refers to a location on the device that is farthest from the clinician using the device and closest to the patient in connection with whom the device is used when the device is used in its normal operation. For example, the distal region of a needle will be the region of the needle containing the needle tip which is to be inserted e.g. into a patient's vein.

As used herein, the term "in" or "inwardly" or "inner" refers to a location with respect to the device that, during normal use, is the inside of the device. Conversely, as used herein, the term "out" or "outwardly" or "outer" refers to a location with respect to the device that, during normal use, is toward the outside of the device.

As used herein, the terms first, second, third, etc. are understood to describe different structures/elements so as to distinguish one from another. However, the terms are not structurally limiting unless the context indicates otherwise.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

As used herein "ready position" means the huber needle is ready to be inserted into subcutaneously implanted ports for insertion or infusion of fluids.

As used herein "locked position" means the huber needle is safely guarded once the needle is retrieved from the subcutaneous port.

Referring now to FIG. 1, it illustrates a huber needle assembly according to one of the embodiments of the present invention. The huber needle assembly having a safety mechanism comprising a main body 10, the main body 10 comprising a needle hub 12 and a base 14, the needle hub having a distal end 28 and a proximal end 30, a huber needle 16 with a needle tip 18, the huber needle 16 is slidably disposed across the needle hub 12 through a needle fitment area 17, a wing holder 20 at the base 12 having two wings 22 at both the sides of the wing holder 20 opposing each other, a conduit 33 through which an axle 32 is placed to connect the base 14 with the needle hub 12, a connector 24 is slidably arranged across the space 26 provided between the distal end 28 and the proximal end 30 of the needle hub 12 through a lever 36 and across the chamber 48 of the base 14 through a lever 37 (not shown), the dimension of the space 26 is according to the length of the connector 24, so that the connector 24 is axially arranged across the space 26 of the needle hub 12 at the ready position of the huber needle 16, the distal end 28 of the needle hub 12 having a flip 34.

The connector 24 connect the needle hub 12 and the base 14. The proximal end of the needle hub 12 having a channel 38 through which a tube 40 is fitted which is used for infusion of fluids. The one end of the tube 40 is connected to the proximal end 30 of the needle hub 12 and the other end of the tube 40 is connected to a luer lock 42, the luer lock 42 having female luer 44 in order to make leak-free connections between two parts. The tube 40 has a clamp 46 to regulate the flow of liquid through the tube 40.

The two wings 22 are made up of soft material which are attached at the wing holder to provide comfortable contact and hinge connection with needle hub 12 and connector 24. The wings 22 can be pivoted up to be grasped by in the fingers of a clinician, or pivoted downward to be applied on the skin of the patient. In some implementations, the wings 22 have a groove structure or texture formed into their upper and/or lower surfaces, to enable better grasping of the wings 22.

In some embodiments, the channel 38 is sized and adapted for a tight fit around the tube 40. In some embodiments, the channel 38 can be formed to have a tolerance around the tube 40 that provides a predetermined coefficient of friction for relative ease or difficulty in sliding the needle hub 12 relative to the tube 40. The luer lock 42 and female luer 44 have 6% tapper fitting. The tapper fitting of the luer lock and female luer can vary according the requirement.

Figure 2:
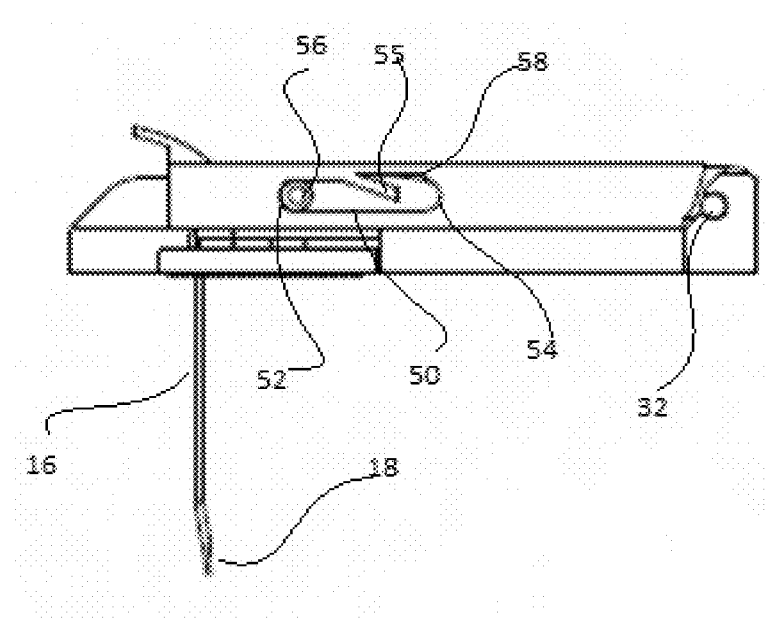
FIG. 2 illustrates the side view of the huber needle assembly in a ready position according to the embodiment of FIG. 1.

Referring to FIG. 2, a side view of the huber needle assembly in a ready position according to embodiment of FIG. 1 is illustrated. It illustrates a position when the huber needle 16 is positioned and inserted into the port for fluid extraction or insertion. At the ready position, the huber needle 16 is at 90° with respect to the base 14 and a sharp distal end that is formed (i.e. bent) and adapted to allow ease of penetration of skin and/or port while minimize coring damage, the connector 24 is axially (A) arranged across the space 26 of the needle hub 12 through the locking shaft 50 of the needle hub 12 with a knob 56. The locking shaft 50 having a first end 52 and a second end 54. The locking shaft 50 has a locking protrusion 55 with a groove 58 across the second end 54 of the locking shaft 50.

Figure 3:
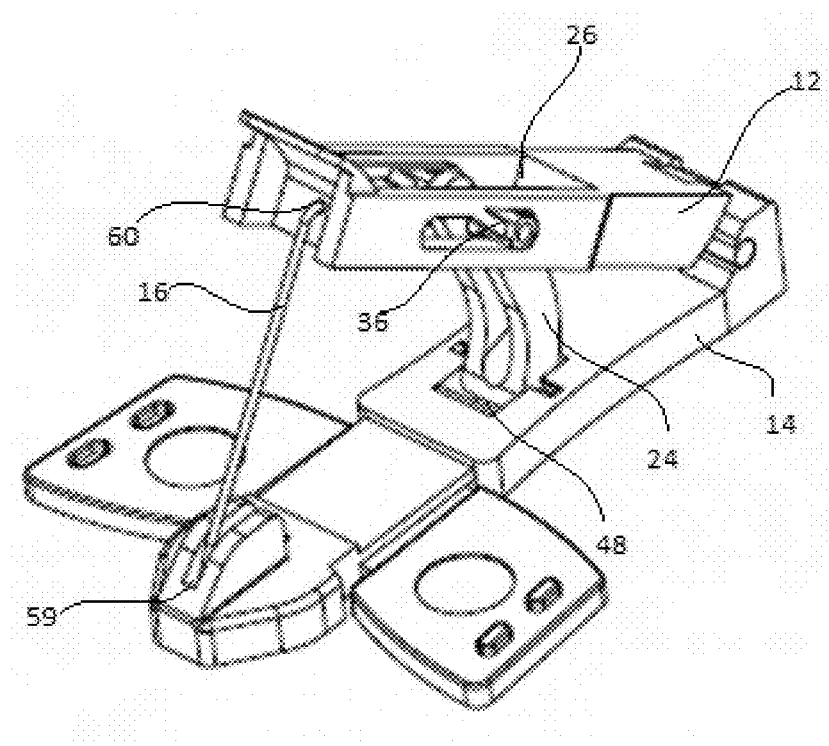
FIG. 3 illustrates the perspective view of the huber needle assembly in a locked position according to the embodiment of FIG. 1.

Referring to FIG. 3, a perspective view of the huber needle assembly in a locked position according to the embodiments of FIG. 1 is illustrated. It illustrates the position when the huber needle 16 is removed from the port and a subsequent protection of the huber needle 16 is made. The huber needle 16 passes through a bore 60 at the distal end of the needle hub 12 across a channel 38 at the proximal end of the needle hub 12 through the needle fitment area 17, the channel 38 is connected to the tube 40 used for infusion of fluids. It shows that when the huber needle is extracted from the port, the huber needle 16 is tilted by 30°-60° with respect to the needle hub 12 and passes through the bore 60 to the channel 38, the connector 24 will slide from first end 52 of the locking shaft 50 to the second end 54 of the locking shaft 50 with the help of lever 36 and lever 37. The knob 56 fixed across the lever 36, the knob 56 will slide according to the position of the lever 36 across the locking shaft 50 and stuck or locked across the groove 58 once the lever 36 locked across the locking protrusion 55. The axle 32 at the proximal end 30 of the needle hub 12 is used to restrict upward motion of the needle hub 12. Once the knob 56 gets locked at the groove 58, the tip 18 of the huber needle 16 gets stuck/locked between an aperture 59 of the wing holder 20.

Figure 4:
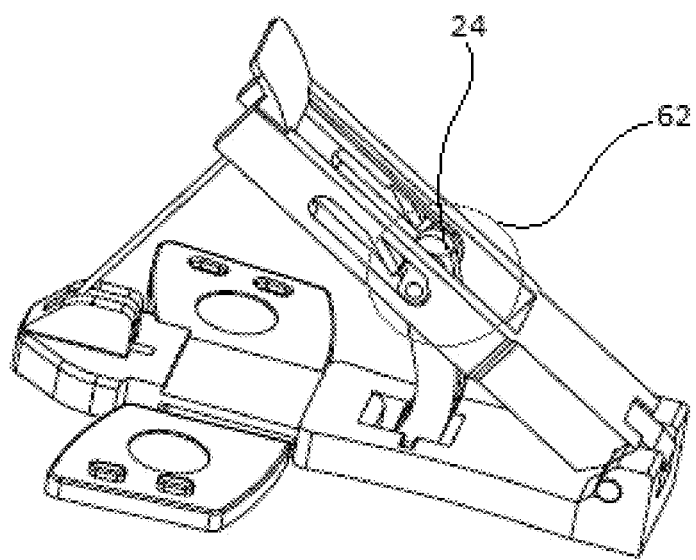
FIG. 4 illustrates the safety mechanism of the huber needle assembly in a safely locked position according to the embodiment of FIG. 1.

Referring to FIG. 4 locking mechanism of the huber needle assembly in a locked position according to the embodiments of FIG. 1 is illustrated. It illustrates the locking mechanism 62 for the safety function of the huber needle 16, which automatically guard the huber needle while retrieving the huber needle from the port through the connector 24. It shows the position of the lever 36 of the connector 24 across the locking protrusion of the locking shaft 50. The huber needle 16 is locked between the aperture 59 of the wing holder 20.

Figure 5A:
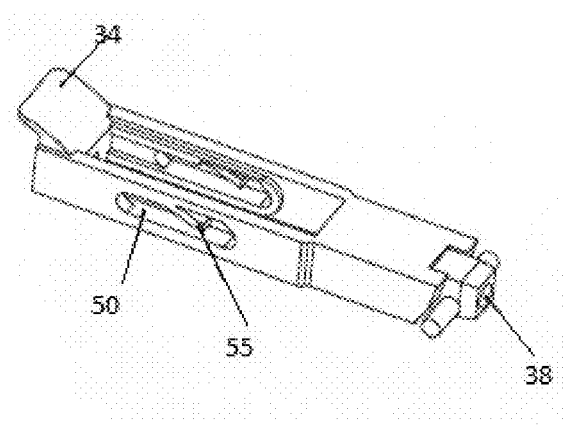
FIG. 5A-5D illustrate the views of needle hub 12 according to the embodiments of FIG. 1.
Figure 5B:
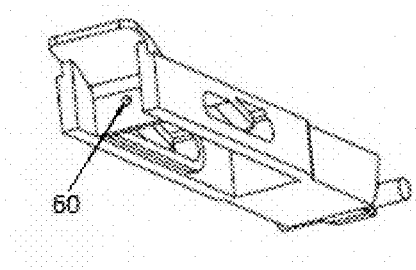
Figure 5C:
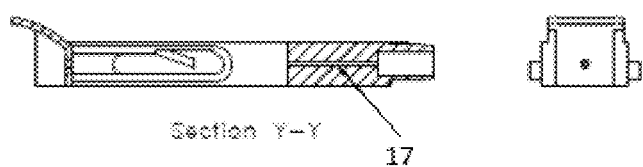
Figure 5D:
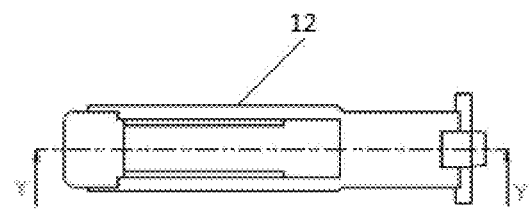

Referring to the FIGS. 5A-5D illustrate the views of needle hub 12 according to the embodiments of FIG. 1. FIG. 5A shows the perspective view of the needle hub 12 having a flip 34 which is used to activate/lift the connector 24, the channel 38 provides fitment area for the tube 40 for infusion of fluids. The locking shaft 50 for sliding the connector having locking protrusion 55 between the first end 52 and second end 54 of the locking shaft 50 which is used to permanently locked with the connector, groove 58 across the second end 54 of the locking shaft 50 which is used to lock the knob 56. FIG. 5B shows another perspective view of the needle hub 12 having a bore 60 through which huber needle passes to the channel. FIG. 5C shows another perspective view of the needle hub 12 which shows the needle fitment across the Y-Section of the needle hub and the tube 40 for passage of fluid. FIG. 5D shows the top view of the needle hub 12. The Y-Section shows the horizontal position of the needle hub.

Figure 6:
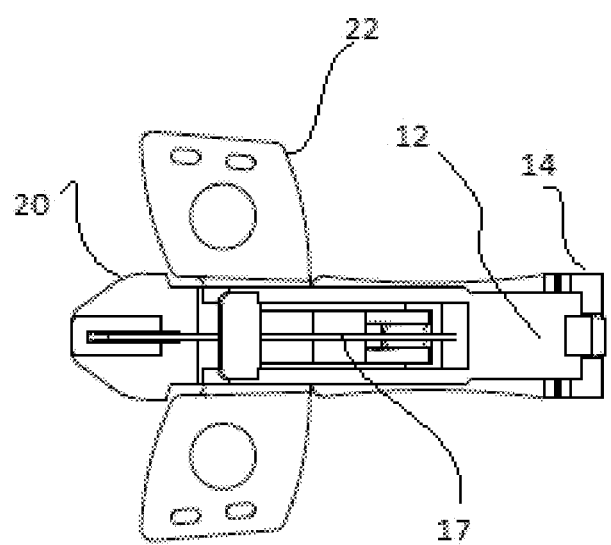
FIG. 6 illustrates the bottom view of the huber needle assembly in a safely locked position according to the embodiment of FIG. 1.

Referring to FIG. 6 a bottom view of the huber needle assembly according to the embodiment of FIG. 1 is illustrated. It shows the bottom view of the main body 10 comprising a needle hub 12 having a space 26 across which connector 24 is attached and a bore 60 through which huber needle 16 passes to the channel 38. The bottom side of the wings 22 at the opposite sides of the wing holder 20. The wing holder works as a shield when safety mechanism activated and the wings 22 provide gripping to hold the needle hub 12 while insertion of huber needle 16 into the port at the subcutaneous area of the skin.

The wings 22 are connected with the wing holder at the base that enables the wings 22 to be bent, rotated, pivoted, flapped or otherwise moved up or down. For instance, two opposing wings 22 can be bent upward to be grasped by the clinician to control the movement, direction, insertion and extraction of the needle attached thereto. In another instance, once the needle is inserted into the skin of the patient, the two wings 22 can be bent downward towards the skin surface of the patient, or onto a patch or other retaining mechanism.

Figure 7:
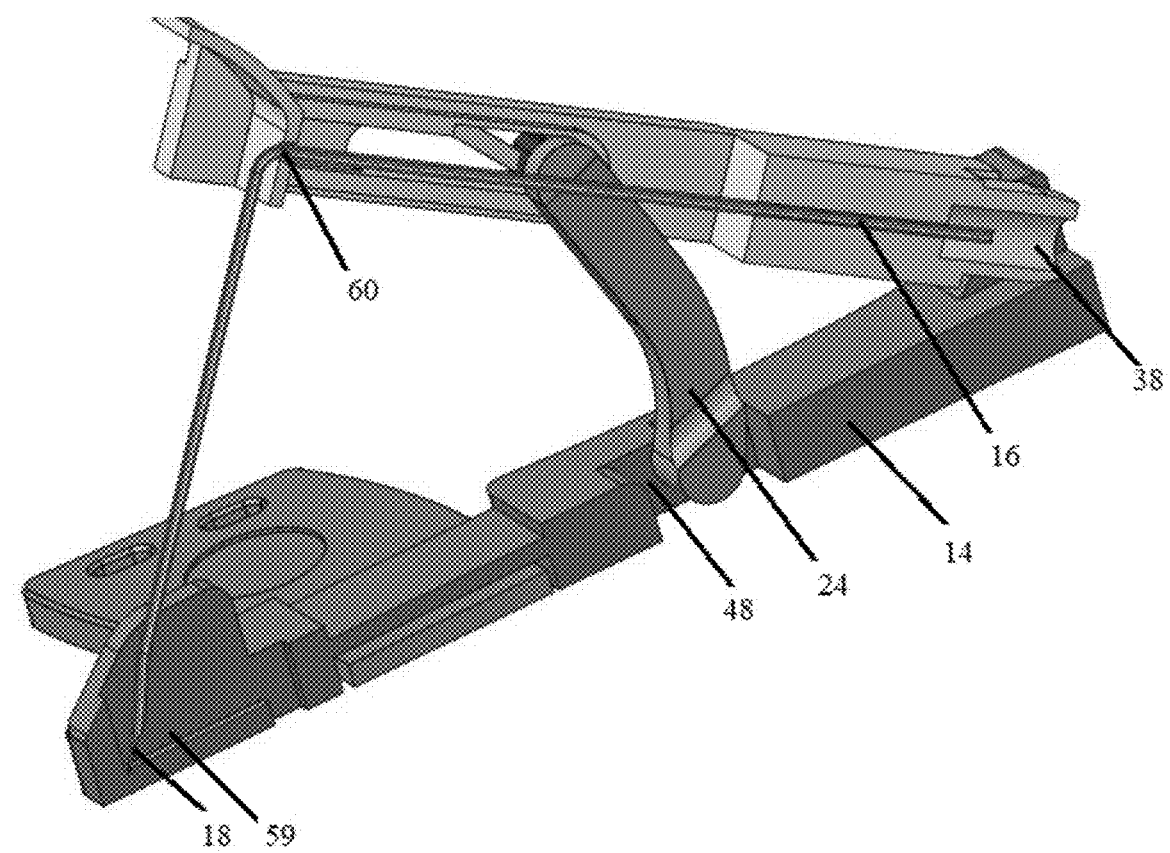
FIG. 7 illustrates a cross-section of the huber needle assembly in a safely locked position according to the embodiment of FIG. 1.

Referring to FIG. 7, it illustrates the cross-sectional view of the huber needle assembly according to the embodiment of FIG. 1. It illustrates the position of the hubber needle 16 at its protected state. The huber needle passes across the bore 60 through the needle fitment area 17 to the channel 38 for infusion of fluid to the tube 40.

Figure 8:
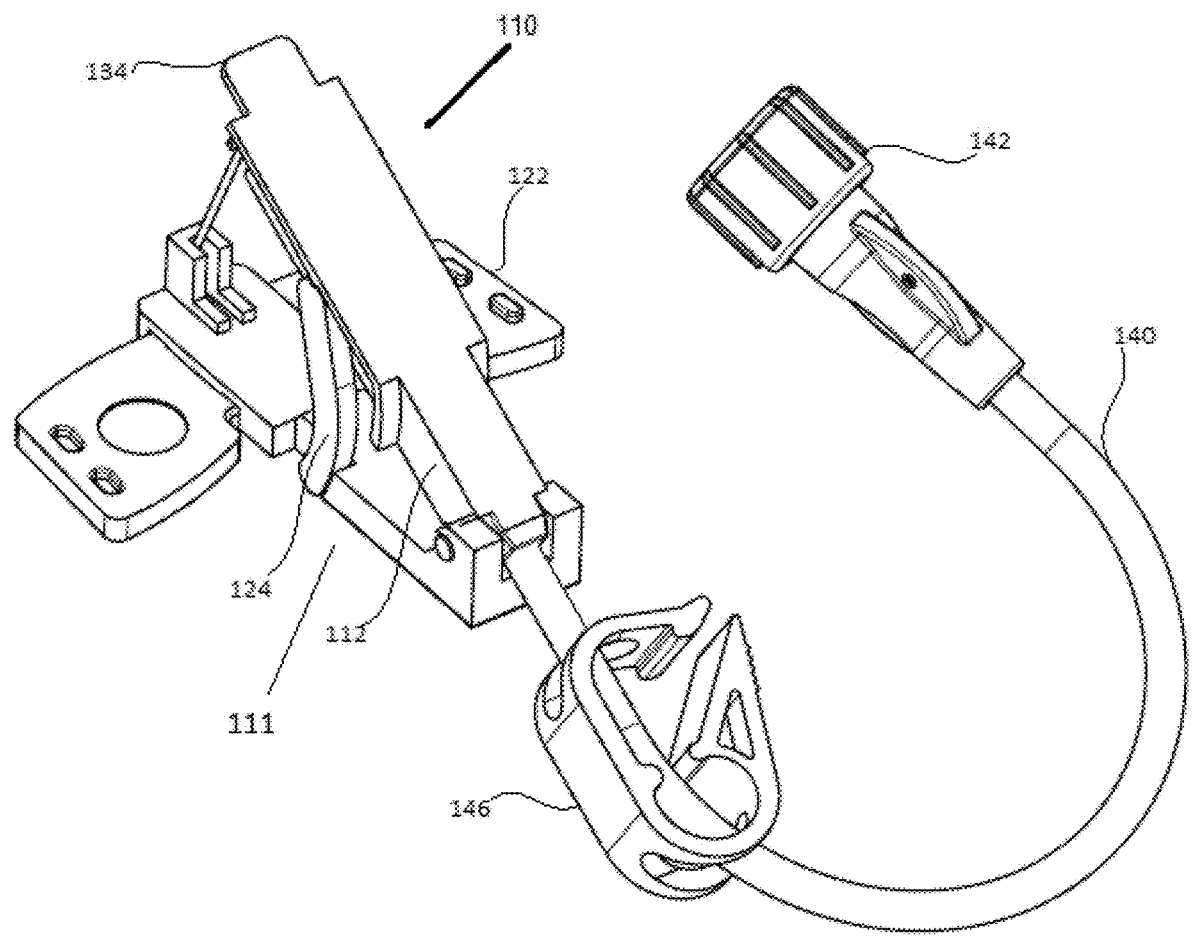
FIG. 8 illustrates a huber needle assembly according to another embodiment of the present invention.

Referring to FIG. 8 a huber needle assembly according to another embodiment of the present invention is illustrated. The main body 110 comprises a huber needle assembly with a safety mechanism for guarding the huber needle tip against accidental pricking. The main body comprising a needle hub 112 and a base 114, a huber needle 116 with a needle tip 118, the needle hub 112 having distal end 128 and a proximal end 130, a needle fitment area 117 between the distal end 28 and proximal end 130 of the needle hub 112 through which huber needle 116 will pass, the distal end 28 of the needle hub 12 having a flip 134, a wing holder 120 having two wings 122 at the both side of the wing holder 120 opposing each other, a conduit 133 through which an axle 132 is placed to connect the base 114 with the needle hub 112.

A connector 124 according to another embodiment of the present invention, which connects the needle hub 112 and base 114. The proximal end of the needle hub 112 having a channel 138 through which needle passes and connected to the tube 140. The one end of the tube 140 is connected to the proximal end 130 of the needle hub 112 and the other end of the tube 140 is connected to a luer lock 142 having female luer 144 in order to make leak-free connections between two parts. The tube 140 has a clamp 146 to regulate the flow of liquid across tube 140.

The two wings 122 are made up of soft material which attached at the wing holder to provide comfortable contact and hinge connection with needle hub 112 and connector 124. The wings 122 can be pivoted up to be grasped by in the fingers of a clinician, or pivoted downward to be applied on the skin of the patient. In some implementations, the wings 122 have a groove structure or texture formed into their upper and/or lower surfaces, to enable better grasping of the wings 122.

In some embodiments, the channel 138 is sized and adapted for a tight fit around the tube 140. In some embodiments, the channel 138 can be formed to have a tolerance around the tube 140 that provides a predetermined coefficient of friction for relative ease or difficulty in sliding the needle hub 112 relative to the tube 140. The luer lock 142 and female luer 144 have 6% tapper fitting. The tapper fitting of the luer lock and female luer can vary according to the requirement.

Figure 9:
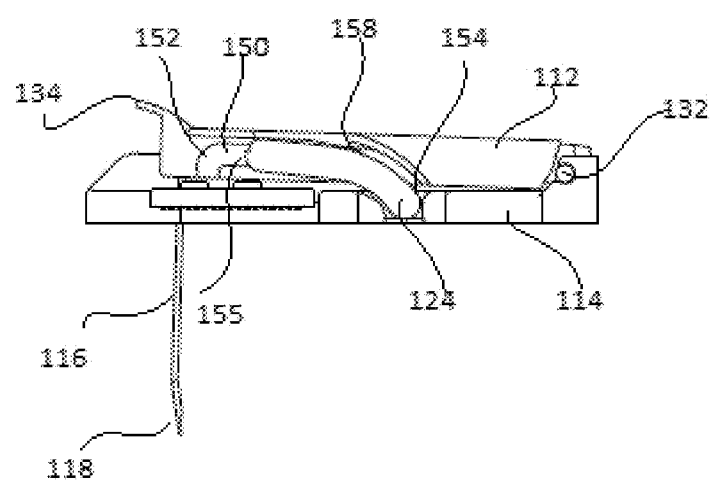
FIG. 9 illustrates the side view of the huber needle assembly in a ready position according to another embodiment of FIG. 8.

Referring to FIG. 9 a side view of the huber needle assembly in a ready position according to another embodiment of FIG. 8 is illustrated. It illustrates the position when the huber needle 116 is positioned and inserted into the port for fluid extraction or insertion. At the ready position, the huber needle 116 is at 90° with respect to the base 114 and a sharp distal end that is formed (i.e. bent) and adapted to allow ease of penetration of skin and/or port while minimizing coring damage, the connector 124 is axially (A) arranged across the locking shaft 150 of the needle hub 112. The locking shaft 150 having first end 152 and second end 154 with a groove 158 across the second end 154 of the locking shaft 150. The connector 124 have locking protrusion 155.

Figure 10:
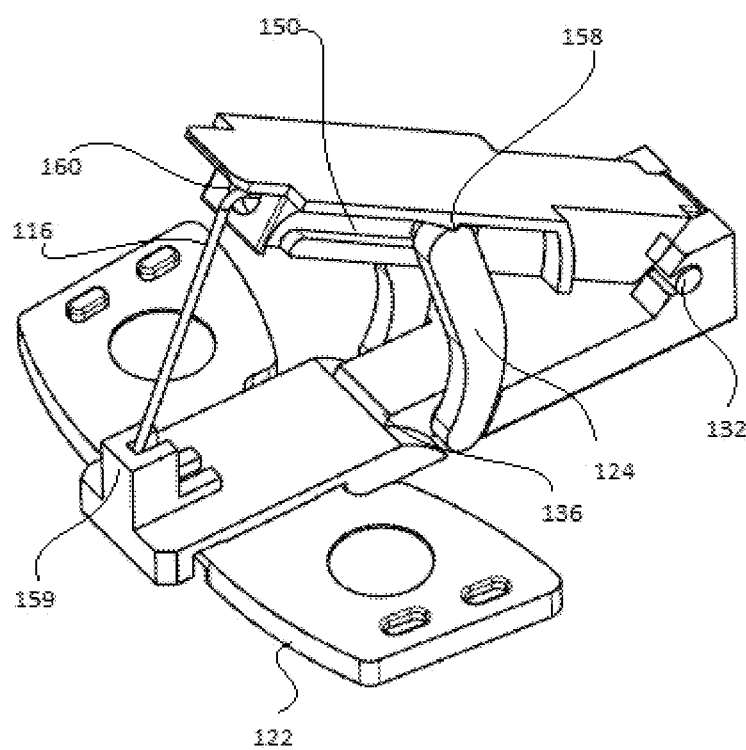
FIG. 10 illustrates the perspective view of the huber needle assembly in a locked position according to another embodiment of FIG. 8.

Referring to FIG. 10 a perspective view of the huber needle assembly in a locked position according to another embodiment of FIG. 8 is illustrated. It illustrates the position when the huber needle 116 is removed from the port and a subsequent protection of the huber needle 116 is made. The connector 124 is slidably arranged across both side of the needle hub 112 through the lever 136 which is attached at the chamber 148 of the base 114. The huber needle 116 passes through a bore 160 at the distal end of the needle hub 112 across a channel 138 at the proximal end of the needle hub 112, the channel is connected to the tube 140 used for infusion of fluids. It shows that when the needle is extracted from the port the huber needle is tilted by 30°-60° with respect to the needle hub 112 and passes through the bore 160 to the channel 138, the connector 124 will slide from first end 152 of the locking shaft 150 to the second end 154 of the locking shaft 150 where the locking protrusion 155 of the connector 124 will be stuck/locked at the groove 158 of the locking shaft 150. The axle 132 at the proximal end 130 of the needle hub 112 is used to restrict upward motion of the needle hub 112. Once the locking protrusion 155 will get locked at the groove 158 and the tip 118 of the huber needle 116 will stuck/locked between an aperture 159 of the wing holder 120.

Figure 11:
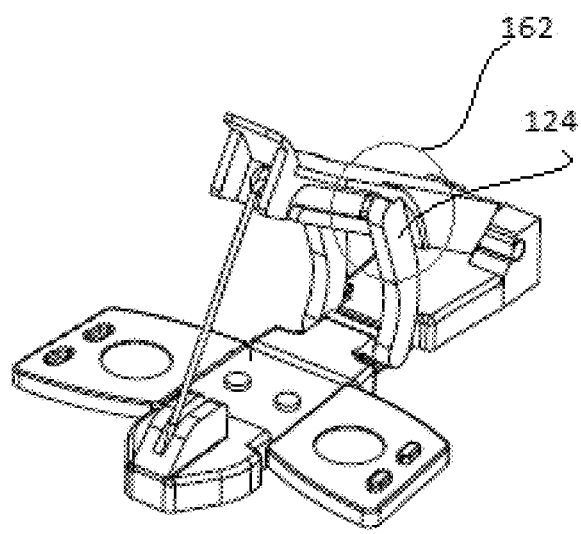
FIG. 11 illustrates the locking mechanism of the huber needle assembly in a locked position according to other embodiments of FIG. 8.

Referring to FIG. 11 locking mechanism of the huber needle assembly in a locked position according to another embodiments of FIG. 8 is illustrated. It illustrates the locking mechanism 162 for the safety function of the huber needle 116, which automatically guard the huber needle 116 while retrieving the huber needle from the port through the connector 124. It shows the position of the locking protrusion 155 of the connector 124 across the groove 154 of the locking shaft 150. The needle is locked between the aperture 159 of the wing holder 20.

Figure 12A:
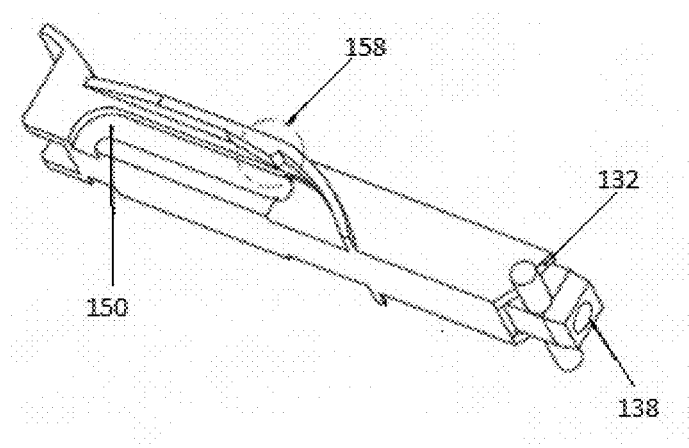
FIG. 12A-12D illustrate the views of needle hub 112 according to another embodiment of FIG. 8.
Figure 12B:
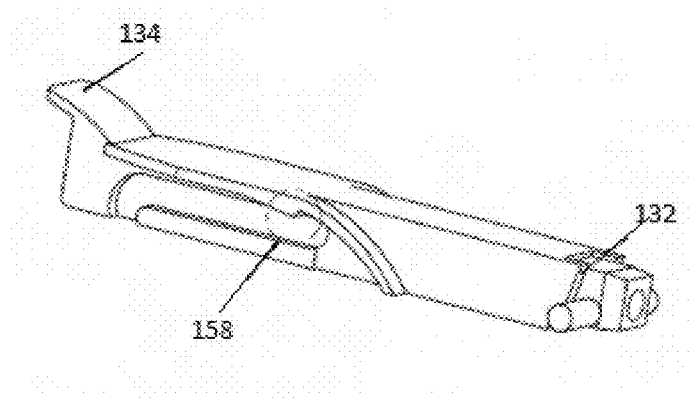
Figure 12C:
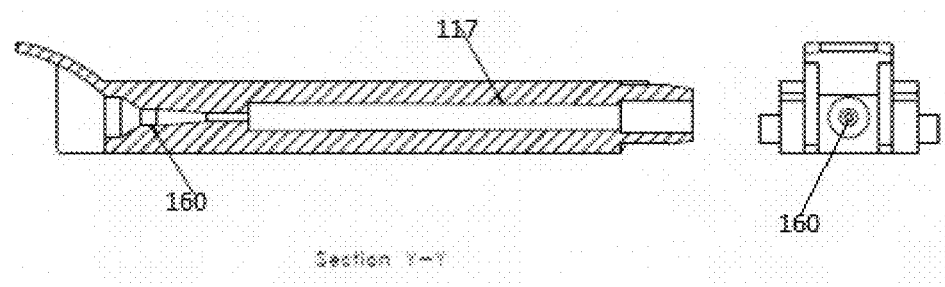
Figure 12D:
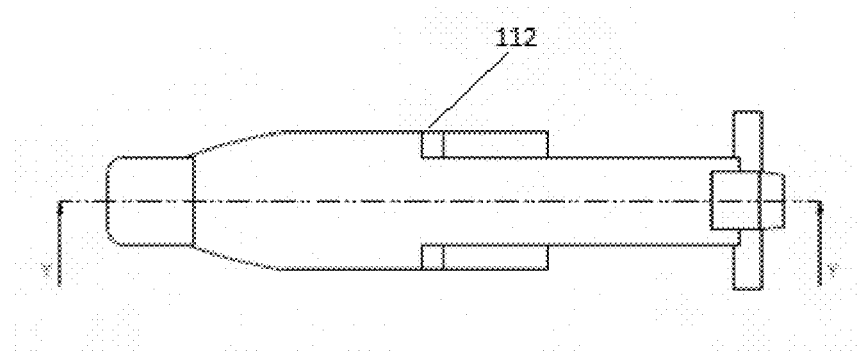

Referring to the FIGS. 12A-12D, they illustrate the views of needle hub 112 according to another embodiment of FIG. 8. FIG. 12A shows the perspective view of the needle hub 112 having a channel 38 providing fitment area to the tube 40 for infusion of fluids. The locking shaft 150 having first end 152 and second end 154, groove 158 across the second end 154 of the locking shaft 150 which is used to permanently lock the connector 124. FIG. 12B shows another perspective view of the needle hub 112 having a flip 134 which is used to activate/lift the connector 24. FIG. 12C shows another perspective view of the needle hub 112 which shows the needle fitment area 117 horizontally (Y-Section) across the needle hub 112 and the tube 140 for passage of fluid. FIG. 12D shows the top view of the needle hub 112. The Y-Section shows the horizontal position of the needle hub.

Figure 13:
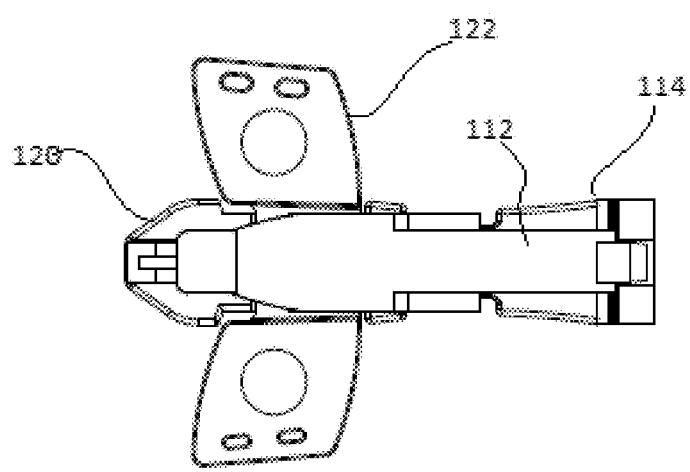
FIG. 13 illustrates the top view of the huber needle assembly in a locked position according to one of the embodiments of FIG. 8.

Referring to FIG. 13 a top view of the huber needle assembly in a locked position according to another embodiments of FIG. 8 is illustrated. It shows the top view of the main body 110 comprising the needle hub 112 and the wings 122 at the opposite sides of the wing holder 120. The wing holder works as a shield when safety mechanism activated and the wings 122 provide gripping to hold the needle hub 112 while insertion of huber needle 116 into the port at the subcutaneous area of the skin.

The wings 22 are connected with the wing holder at the base that enables the wings 22 to be bent, rotated, pivoted, flapped or otherwise moved up or down. For instance, two opposing wings 22 can be bent upward to be grasped by the clinician to control the movement, direction, insertion and extraction of the needle attached thereto. In another instance, once the needle is inserted into the skin of the patient, the two wings 22 can be bent downward towards the skin surface of the patient, or onto a patch or other retaining mechanism.

Figure 14:
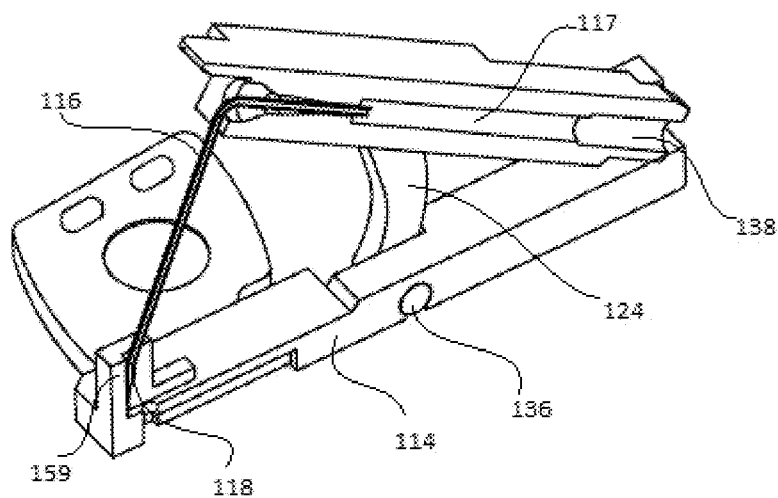
FIG. 14 illustrates the cross-sectional view of the huber needle assembly in a locked position according to another embodiments of FIG. 8.

Referring to FIG. 14, it illustrates the cross-sectional view of the huber needle assembly according to another embodiments of FIG. 8. It illustrate the position of the hubber needle at its protected state. The huber needle passes through the bore 160 to the channel 138 for infusion of fluid to the tube 140.

Figure 15:
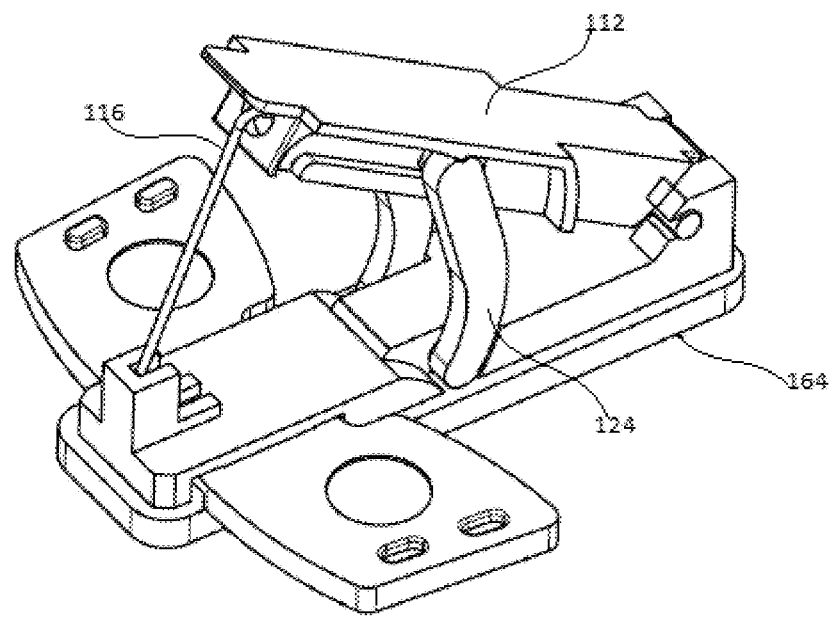
FIG. 15 illustrates the perspective view of the huber needle assembly with foam pad according to another embodiment of FIG. 8.

Referring to FIG. 15 the perspective view of the huber needle assembly with foam pad according to another embodiment of FIG. 8 is illustrated. The top of the base 114 is covered with a foam pad 164, which is a non-absorbent foam pad, the foam pad is designed to assist with the placement of the huber needle 116 into the port for fluid extraction or insertion the base 114 with comfort of the patient and closed cell materials are designed to help reduce the risk of needlestick injuries, bacterial exchange and compression.

The construction and shape of the huber needle assembly having a safety mechanism according to the various embodiments of the present disclosure provides a simple configuration. The simple and compact design of the huber needle assembly having safety mechanism according to the above disclosure is advantageous in a clinical setting because it provides an automatic protection against accidental pricking by the needle tip thereby reducing injury or discomfort to a patient and provides better safety features. In addition, such design greatly reduces manufacturing costs and is efficient, effective and simple in its construction and use.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the spirit or scope of the invention as set forth in the claims.

The scope of the present invention herein disclosed is not limited by the particular disclosed embodiments described above but determined only by a fair reading of the complete specification to be filed on this application.

LIST OF REFERENCE NUMERALS 10, 110 main body
11, 111 huber needle assembly
12, 112 needle Hub
14, 114 base
16, 116 huber Needle
17, 117 needle fitment area
18, 118 huber Needle Tip
20, 120 wing Holder
22, 122 wing(s)
24, 124 connector
26 space
28, 128 distal end
30, 130 proximal end
32, 132 axle
33, 133 conduit
34, 134 flip
36, 136 lever
37 lever
38, 138 channel
40, 140 tube
42, 142 luer lock
44, 144 female luer
46, 146 clamp
48, 148 chamber
50, 150 locking shaft
52, 152 first end
54, 154 second end
56 knob
55, 155 locking protrusion
58, 158 groove
59, 159 aperture
60, 160 bore
62, 162 locking mechanism
164 foam pad
A axially
Y horizontally

The invention claimed is:

1. A safety mechanism for a huber needle assembly comprising:
   a main body having a needle hub and a base;
   a huber needle disposed along the needle hub with a tip wherein a proximal end of the needle hub is movably attached to a proximal end of the base;
   a wing holder at a distal end of the base, the wing holder having two sides and a wing extending from each side;
   a connector slidably arranged across a space provided between a distal end of the needle hub and the proximal end of the needle hub through a first lever at a distal end of the connector wherein a proximal end of the connector is movably connected to the base through a second lever; and
   wherein said needle hub comprises a flip to activate the connector and a locking shaft across the space, wherein the locking shaft comprises a first end and a second end; and
   a locking protrusion with a groove across the second end of the locking shaft, wherein while retracting the huber needle, the connector slides from the first end of the locking shaft to the second end of the locking shaft with the help of the first lever at the distal end of the connector and the second lever at the proximal end of the connector;
   a knob fixed across the first lever at the distal end of the connector gets locked at the groove once the first lever at the distal end of the connector is locked across the locking protrusion; and
   the tip of the huber needle gets locked between an aperture of the wing holder.

2. The safety mechanism for a huber needle assembly as claimed in claim 1, wherein a dimension of the space is according to the length of the connector.

3. The safety mechanism for a huber needle assembly as claimed in claim 1, further comprising an axle at the proximal end of the needle hub and wherein the axle at the proximal end of the needle hub is used to restrict upward motion of the needle hub.

4. The safety mechanism for a huber needle assembly as claimed in claim 1, further comprising a port and wherein the huber needle is tilted by 30°-60° while retracting from the port.

5. The safety mechanism for a huber needle assembly as claimed in claim 4, further comprising an axle at the proximal end of the needle hub and wherein the axle at the proximal end of the needle hub is used to restrict upward motion of the needle hub.

6. The safety mechanism for a huber needle assembly as claimed in claim 1, further comprising a needle fitment area and wherein a bore at the distal end of the needle hub is connected to a channel allowing the huber needle to pass through the needle fitment area.

7. A safety mechanism for a huber needle assembly comprising:
   a main body having a needle hub and a base;
   a huber needle disposed along the needle hub with a tip wherein a proximal end of the needle hub is movably attached to a proximal end of the base;
   a wing holder at a distal end of the base, the wing holder having two sides and a wing extending from each side;
   a lever movably connected to the base;
   a connector slidably arranged across both sides of the needle hub through lever;
   wherein said needle hub comprises a flip to activate the connector and a locking shaft, wherein the locking shaft comprises a first end and a second end; and
   a groove across the second end of the locking shaft;
   wherein while retracting the huber needle, the connector slides from the first end of the locking shaft to the second end of the locking shaft with the help of the lever;
   the connector has a locking protrusion, the locking protrusion of the connector gets locked at the groove; and
   the tip of the huber needle gets locked between an aperture of the base.

8. The safety mechanism for a huber needle assembly as claimed in claim 7, further comprising a needle fitment area and wherein a bore at a distal end of the needle hub is connected to a channel allowing the huber needle to pass through the needle fitment area.

9. The safety mechanism for a huber needle assembly as claimed in claim 7, further comprising a port and wherein the huber needle is tilted by 30°-60° while retracting from the port.

10. The safety mechanism for a huber needle assembly as claimed in claim 7, wherein the base is covered with a foam pad to provide comfort to a patient and reduce risk of needlestick injuries, bacterial exchange and compression.

* * * * *

UNITED STATES PATENT AND TRADEMARK OFFICE
CERTIFICATE OF CORRECTION

PATENT NO. : 12,397,106 B2  
APPLICATION NO. : 17/419007  
DATED : August 26, 2025  
INVENTOR(S) : Rishi Baid et al.

Page 1 of 1

It is certified that error appears in the above-identified patent and that said Letters Patent is hereby corrected as shown below:

In the Claims

Column 10, Line 39, in Claim 7 please replace "needle hub through lever;" with --needle hub through the lever;--

Signed and Sealed this  
Thirtieth Day of September, 2025

John A. Squires  
*Director of the United States Patent and Trademark Office*